United States Patent [19]

Landry

[11] Patent Number: 5,736,343
[45] Date of Patent: Apr. 7, 1998

[54] DETECTION OF ORGANIC COMPOUNDS THROUGH REGULATION OF ANTIBODY-CATALYZED REACTIONS

[76] Inventor: Donald Landry, 29 Chremount Apt. 2 South, New York, N.Y. 10027

[21] Appl. No.: 698,812

[22] Filed: Aug. 16, 1996

Related U.S. Application Data

[60] Provisional application No. 60/002,466, Aug. 16, 1995.
[51] Int. Cl.⁶ .................................................. C12Q 1/25
[52] U.S. Cl. ............................... 475/7.6; 435/188.5
[58] Field of Search .......................... 435/7.6, 188.5

[56] References Cited

U.S. PATENT DOCUMENTS

| | | | |
|---|---|---|---|
| 3,551,555 | 12/1970 | Hermanus et al. | 424/12 |
| 3,720,760 | 3/1973 | Hennich et al. | 424/1 |
| 3,811,840 | 5/1974 | Bauer et al. | 23/253 |
| 3,867,517 | 2/1975 | Ling | 424/1 |
| 3,893,808 | 7/1975 | Campbell | 23/253 |
| 3,901,657 | 8/1975 | Lightfoot | 23/253 |
| 3,926,564 | 12/1975 | Giaever | 23/254 |
| 3,932,220 | 1/1976 | Liotta | 195/103.5 |
| 3,933,997 | 1/1976 | Hersh et al. | 424/1 |
| 3,935,074 | 1/1976 | Rubenstein et al. | 195/103.5 |
| 3,949,064 | 4/1976 | Bornstein et al. | 424/1 |
| 3,960,499 | 6/1976 | White | 25/257 |
| 3,961,894 | 6/1976 | Gordon et al. | 23/230.6 |
| 3,975,162 | 8/1976 | Renn | 23/253 |
| 3,979,509 | 9/1976 | Giaever | 424/12 |
| 3,981,981 | 9/1976 | Reunanen | 424/1.5 |
| 3,989,591 | 11/1976 | Liotta | 195/1.8 |
| 4,012,198 | 3/1977 | Finter et al. | 23/253 |
| 4,016,043 | 4/1977 | Schuurs et al. | 195/103.5 |
| 4,017,597 | 4/1977 | Reynolds | 424/1.5 |
| 4,020,151 | 4/1977 | Bolz et al. | 424/1.5 |
| 4,038,485 | 7/1977 | Johnston et al. | 23/270 |
| 4,144,306 | 3/1979 | Figueras | 422/56 |
| 4,175,923 | 11/1979 | Friend | 23/270 |
| 4,205,952 | 6/1980 | Cais | 23/230 |
| 4,235,601 | 11/1980 | Deutsch et al. | 23/230 |
| 4,659,567 | 4/1987 | Tramontano et al. | 424/85 |
| 4,792,446 | 12/1988 | Kim et al. | 424/85 |
| 4,888,281 | 12/1989 | Schochetman et al. | 435/72 |
| 4,963,355 | 10/1990 | Kim et al. | 424/85.8 |
| 5,030,717 | 7/1991 | Tramontano et al. | 530/387 |
| 5,037,750 | 8/1991 | Schochetman et al. | 435/183 |
| 5,187,086 | 2/1993 | Janda | 435/140 |

FOREIGN PATENT DOCUMENTS

WO 89/05977 6/1989 WIPO.

*Primary Examiner*—Charles L. Patterson, Jr.

[57] ABSTRACT

The present invention provides a method for determining the presence of a target organic molecule in a sample which comprises either (A): first, adding a substrate molecule to the sample, the substrate molecule being a conjugate of the target organic molecule and a reporter molecule; second, adding a catalytic monoclonal antibody to the sample which (1) recognizes and binds the target organic molecule when the target organic molecule is present in the sample and (2) recognizes and binds the substrate molecule when the target organic molecule is not present in the sample; and third detecting a change in the sample signifying the absence of the target organic molecule, the change being the product of an antibody-catalyzed reaction and thereby determining the presence of an organic molecule in the sample; or (B): first adding a substrate molecule to the sample, the substrate molecule being a conjugate of a molecule complementary to the target molecule and a reporter molecule; second adding a catalytic monoclonal antibody to the sample which (1) recognizes and binds the target organic molecule when the target molecule is present in the sample and (2) recognizes and binds the substrate molecule only if the target molecule is present in the sample; and third detecting a change in the sample signifying the presence of the target molecule, the change being the product of an antibody-catalyzed reaction and thereby determining the presence of the target organic molecule in the sample.

25 Claims, 8 Drawing Sheets

REPORTER -OR

REPORTER -O
(higher ε, right-shifted lambda$_{max}$)

$H_2N$—TTL—NH—CH—C(=O)—PTIAG
|
$CH_2$
|
$CH_2$
|
C(=O)—$NH_2$

AA $H_2N$—TTL—NH—CH—C(=O)—PTIAG
|
$CH_2$
|
$CH_2$
|
C(=O)—O—(2-CN, 4-$NO_2$ phenyl)

BB $H_2N$—TTL—NH—CH—C(=O)—PTIAG
|
$CH_2$
|
$CH_2$
|
O=P(—$O^-$)—O—(2-CN, 4-$NO_2$ phenyl)

CC

MOMP FRAGMENT SERVES AS CARRIER PROTEIN

FIGURE 5

MOMP FRAGMENT SERVES AS CARRIER PROTEIN

AAA

BBB

CCC

DETECTION OF ORGANIC COMPOUNDS THROUGH REGULATION OF ANTIBODY-CATALYZED REACTIONS

This application claims the priority of a provisional application having U.S. Ser. No. 60/002,466, filed Aug. 18, 1995 which is incorporated by reference herein.

BACKGROUND OF THE INVENTION

Antibodies have significant use in diagnostic immunoassays, i.e., assays which depend on the specific interaction between an antigen and a corresponding antibody. The use of immunoassays as a means of determining the presence and/or amount of a target molecule (generally a clinically important molecule) is well known.

Enzymes also have significant use in diagnostic assays. The enzyme binds and transforms the target and the products of the reaction provide the means of detection. Although relatively few clinically important molecules are susceptible to a colorimetric reaction with a commercially available enzyme, those that are susceptible, e.g. glucose, can be assayed by simple and convenient dipstick methodology (1–12).

The ability of antibodies to functionally mimic enzymes and mediate catalysis is well known. A variety of chemical transformations have been catalyzed by antibodies raised to a transition-state analog of the substrate (13–22). The best studied of these reactions, and one of the few reaction types with instances of rates of reaction approaching those of natural enzymes, is the antibody-catalyzed hydrolysis of activated ester moieties (13, 14, 23–33).

Before applicant's invention no one had capitalized on the use of antibody-catalyzed reactions in a generally useful diagnostic immunoassay. The reasons are clear. First, although antibody-catalyzed reaction of a target molecule has been proposed as the basis of a detection method (34), most targets are not susceptible to any known antibody-catalyzed reaction. Second, although a small subset of targets are susceptible to some type of antibody-catalyzed reaction, the majority of such reaction types are catalyzed at less than useful rates. Third, although relatively rarely a target molecule is susceptible to a reaction type (e.g. ester hydrolysis) with the potential for a useful rate of reaction, the product(s) of such a reaction are very rarely detectable by a simple assay. Fourth, no clinically important target molecule is an activated substrate especially predisposed to rapid reaction. Finally, antibody-catalyzed reactions are frequently hampered by the phenomenon of product inhibition, i.e., the products of the reactions bind strongly to the antibody, blocking further reaction with the substrate.

Product inhibition, although circumvented through a variety of strategies, is still considered an impediment to the practical application of catalytic antibodies (35).

But for the problems discussed above, the use of catalytic antibodies as the basis of a diagnostic immunoassay would be invaluable to detect clinically important target molecules including the presence of specific proteins from *Chlamydia trachomatis*, one of the most common human pathogens, and increased plasma levels of phenylalanine, a finding diagnostic of the disorder phenylketonuria. The capacity of an antibody for selective binding of the target would enhance the specificity of the assay; the capacity of an artificial enzyme for turnover (i.e. a single enzyme molecule transforms many substrate molecules and thus amplifies the signal) would enhance sensitivity.

*CHLAMYDIA TRACHOMATIS*

*Chlamydia trachomatis* is a common sexually transmittal disease. Each year, there are three to four million new cases of Chlamydia in the United States at an annual cost of 1.4 billion (36). Chlamydial infection appears to increase the risk of HIV transmission three to five fold (37).

Although chlamydial infection can be cured reliably and inexpensively, diagnosis is difficult (37). Developing nations are particularly burdened, as diagnostic assays and equipment for detection are expensive, difficult to staff, or unavailable. Thus, the development of a novel, easy-to-use, assay which could be used to detect Chlamydia infection quickly and inexpensively could provide a worldwide solution, allowing for early diagnosis and treatment.

Presently, isolation of the organism in culture, direct examination of specimens for inclusions, or detection of chlamydia antigens by an antibody underlie current detection systems.

Cell Culture

Isolation of Chlamydia in cell culture remains the gold standard for the diagnosis of chlamydial infection. Lymphogranuloma venureum (LGV) strains grow well in many cell lines, but non-LVG strains are fastidious. McCoy or HeLa cells are most commonly used. Pretreatment of culture cells with DEAE dextran, a positively charged molecule, is generally recommended to reduce electrostatic repulsion between tissue cells and elementary bodies. The recovery of non-LVG strains, but not LGV strains, improves with centrifugation of the inoculum prior to plating onto the cell monolayer. Typically, non-LGV strains produce a single inclusion for each viable elementary body that is endocytosed, unlike the LVG strains which spread in the monolayer. Between 40 and 70 hours after inoculation, intracytoplasmic inclusions can be detected by Giemsa, Macchiavelli or Gimenez stains in either cell line. Iodine may be used for McCoy cells. However, immunofluorescent staining with monoclonal antibodies is the most sensitive method for the detection of inclusions in primary cultures.

Inexperienced laboratories may have frequent false-positive results, particularly with the iodine stains. Normal inclusions can be mistaken for pathology by untrained personnel. Although cultures performed in vials are more sensitive, microtiter cultures are less expensive and better suited for laboratories that perform a large number of cultures. Isolation of the antigen is the most sensitive element in the diagnostic procedure. False-negative cultures result from sampling the urethral meatus rather than the endourethra, contaminated swabs, inappropriate transport media, or culture contamination due to rectal and cervical sampling (36).

Direct immunofluorescent-antibody test (DFA)

Isolation or direct detection methods often fail to demonstrate the presence of *Chlamydial trachomatis*. Thus, serologic response may be the only indication of the pathogen. Direct immunofluorescence-antibody test, which uses fixed organisms as the antigen, uses species-specific fluorescein-conjugated monoclonal antibodies to Major Outer Membrane Protein (MOMP) to detect chlamydia in direct smears (38,39). These antibodies can demonstrate that cell-free elementary bodies (EB) that are more prevalent than the intracellular inclusion bodies in urethral, cervical, conjunctival and nasopharyngeal specimens. With training, a high degree of specificity in obtaining elementary bodies is possible, despite their small size (36). However, this assay is technically difficult, subjective, and labor intensive. Artifacts may be interpreted as chlamydial EB's by an inexperienced reader. In addition, only a few laboratories are equipped to do the assay routinely, so samples must be transported to a central facility for analysis (40).

Enzyme Immunoassays (EIA or ELISA)

Enzyme immunoassay utilizes labeled monoclonal or polyclonal antibodies raised against chlamydial lipopolysaccharide to identify inclusions in specimens. Samples are analyzed with the use of spectrophotometer. Many laboratories prefer this method, as it allows for the processing of large numbers of specimens by less intensively trained personnel and for the identification of chlamydial antigen more quickly than culture. However, EIAs for chlamydia detection are generally less sensitive and less specific than culture or fluorescence microscopy. Although effective in cell culture, EIAs are not adequate for the direct detection of elementary bodies (36). Cervical flora (urinary pathogens including group A streptococci, *Acinetobacter calcoaceticus, Escherichia coli, Cardinella vaginalis, Neisseria gonorrhoea*, group B streptococci, *Klebsiella pneumoniae*), fecal matter, or Fc-mediated binding of immunoglobulins to *Staphylococcus aureus* have been reported to interfere with the assay, primarily by cross-reactivity (41–44). Although these tests have been reported to perform well in high risk populations and symptomatic patients, the predictive value of EIAs are directly related to the number of inclusions found in culture, compromising sensitivity in groups of patients with low prevalence of infection or those who are asymptomatic. At the present time, its use is recommended for specimens from sites other than the cervix and urethra (36).

DNA Hybridization

Single stranded DNA complementary to the rRNA of *Chlamydia trachomatis* is labeled with acridininm ester and used as a probe. After several incubation and washing steps, the sample is magnetically separated and read with the aid of a luminometer (38). Due to low sensitivity, this assay is not recommended for sample from patients who have a low to moderate risk for infection.

PKU

Another clinically important target molecule is phenylalanine. A high concentration of phenylalanine is indicative of Phenylketonuria (PKU), an inborn error in the metabolism of phenylalanine that affects 1 in 10,000 newborns.

Classic phenylketonurics appear normal at birth but, if left untreated, mental retardation is severe by age one. An estimated one percent of all patients institutionalized for mental impairment have PKU. Life expectancy of untreated phenylketonurics is drastically reduced with a mortality rate of 50% by the age of twenty and 75% by the age of thirty (45).

Early diagnosis of phenylketonuria is essential since irreversible retardation can be prevented. Phenylalanine is an essential amino acid and dietary restriction of phenylalanine diminishes levels and prevents retardation (46). Because uncontrolled hyperphenylalaninemia results in brain damage throughout childhood (and perhaps into adulthood), dietary restriction is recommended to continue indefinitely (47). The effectiveness of dietary restriction can be reliably monitored only by assay of phenylalanine in plasma. An effective prescription for classic PKU includes a synthetic diet low in phenylalanine instituted prior to 4 weeks of age. Dietary management begun after the onset of central nervous system damage will not reverse retardation but may lead to an improvement in behavior (48,49).

Newborn screening is mandatory in the United States but newborns are typically tested only once, just prior to hospital discharge. Newborns with PKU increasingly escape detection on the initial screening test and this trend relates to the need for adequate protein consumption in order to manifest the defect. Thus, detection may be missed if testing occurs too early, as frequently happens due to the recent trend towards early hospital discharge. Also, newborns are increasingly taking breast milk which has a relatively low protein content for the first few post-natal days (50). Infants delivered by Cesarean section are frequently not included in routine newborn care, and may not be tested for the disease (36). In addition, the available screening assays for hyperphenylalaninemia are specific (99.9%) but not sensitive (46). Sensitivity is dependent upon the age at which the testing is implemented and the threshold for a positive test is set. At less than 24 hours of age and with a 4 mg/dL cutoff, 16% of infants with PKU will be missed. At 24 to 48 hours of age, 2.2% will be missed. Presently, rescreening at 2 to 4 weeks is not considered cost effective (48).

Classic PKU, as described above, constitutes approximately half of all patients with hyperphenylalaninemia. Benign hyperphenylalaninemia corresponds to a partial deficiency of phenylalanine hydroxylase and constitutes the other half of PKU patients. Due to less severely elevated levels of phenylalanine, this disorder does not result in the clinical manifestations of classic phenylketonuria. Safe concentrations of blood phenylalanine may be maintained with either a less strict diet or no dietary management. Thus, approximately 99% of all patients with hyperphenylalaninemia would benefit by easy monitoring of blood levels. The remaining one percent of cases of hyperphenylalaninemia are caused by a deficiency of tetrahydrobiopterin (BH4), an essential cofactor for phenylalanine metabolism. This deficiency reflects a defect in one of the enzymes involving $BH_4$ synthesis or metabolism: dihydrobiopterin synthetase (malignant hyperphenylalaninemia I), dihydropteridine reductase (malignant hyperphenylalaninemia II), or guanosine triphosphate cyclohydrolase (malignant hyperphenylalaninemia III). Serum phenylalanine levels in these conditions rise to levels greater than 20 mg/dl (51). Since $BH_4$ is also essential for the synthesis of neurotransmitters such as catecholamines, serotom, 5-hydroxyindole acetic acid and for the maintenance of normal neurological function, patients deficient in $BH_4$ cofactor do not respond to a low phenylalanine diet. Despite early diagnosis and supplementation with L-dopa and 5-hydroxy-tryptophan, seizures in cofactor deficient patients appear early, followed by progressive cerebral and basal ganglia dysfunction and death within a few years (47). The rare patients with hyperphenylalaninemia secondary to $BH_4$ deficiency would fail to benefit by an improvement in monitoring.

A major problem for prevention programs is the relatively new phenomenon of maternal hyperphenylalaninemia (47). With the advent of nutritional therapy, PKU patients have reached reproductive maturity and 92% of the genetically normal offspring of women with PKU not treated with a restricted diet will manifest mental retardation. IQ scores of these offspring have been found to correlate inversely with the maternal phenylalanine level at term and with high levels, microencephaly, congenital heart disease, and seizures are common. Dietary restriction can ameliorate, if not prevent, this adverse outcome if instituted prior to or very early in pregnancy.

A simple dipstick assay could facilitate diagnosis of PKU infants who would otherwise be missed. A quick and inexpensive method would permit repetitive testing which enhances sensitivity. Also, the simplicity and economy of the detection system would allow for the routine diagnosis of PKU in the pediatric office during follow-up care after the infant has consumed sufficient protein to fully manifest the defect. In addition, a catalytic antibody dipstick assay would also enable monitoring of phenylalanine levels in patients undergoing long-term dietary care, a critical application not heretofore feasible. A new addition to this latter group are pregnant women with PKU whose normal unborn babies are placed at risk by maternal hyperphenylalaninemia.

The standard screening assays for hyperphenylalaninemia are a bacterial inhibition assay and a fluorescent assay. Colorimetric tests can also screen for PKU. Thin-layer chromatography (TLC) and high-performance liquid chromatography (HPLC) are generally used to confirm the "positive" PKU results of other assays. HPLC is employed to monitor phenylalanine blood levels by those undergoing long-term dietary management. A brief critique of current assays available for the detection of PKU follows:

Guthrie Bacterial Inhibition Test

In 1961, Robert Guthrie developed a semi-quantitative bacteriologic inhibition assay for phenylalanine. An unmeasured quantity of blood is obtained by heel puncture, collected on filter paper, and placed on a bacterial culture. Beta-2-thienylalanine, incorporated in the agar culture medium, acts as a competitive inhibitor of phenylalanine utilization and inhibits normal bacterial growth of *Bacillus subtilis* (50). The high levels of phenylalanine in a sample from a patient with PKU will overcome phenylalanine inhibition and bacterial growth is observed as an indicator for the disease.

The Guthrie bacterial inhibition test is still the most widely used assay for screening PKU, due to its simplicity and relatively low cost (49). Although the sample is easy to collect and stable during mailing to the laboratory, the assay is time-consuming and may yield false-negative results (49). Infants treated with intravenous antibiotics may have a sufficient concentration to impair bacterial growth. Topical antimicrobial agents used to sterilize the area in which a sample will be taken, can also interfere with the accuracy of the Guthrie assay.

Fluorometric Method

The automated fluorometric method is more precise and quantitative than the Guthrie assay. Phenylalanine is eluted from blood dried on a filter paper disc with 0.2 ml of methanol. After shaking for 15 minutes, the disc is discarded and 0.20 ml of a reagent comprised of succinate buffer, ninhydrin and L-leucyl-L-alanine at pH 5.8 is added. The mixture is then placed in a 60 degrees Celsius water bath for 80 minutes, and cooled to room temperature. 2.5 ml of copper reagent, consisting of sodium carbonate, potassium sodium tartrate and copper sulfate, is then added. This solution is placed in a water bath at 20–30 degrees Celsius for 10–20 minutes. Under these conditions, phenylalanine yields a fluorescent product that is stable for one hour, having activation and emissions peaks of 382 and 490 m$\mu$, respectively (52).

To improve the sensitivity of this assay, large samples of plasma or serum are required. The assay is very sensitive to pH and this sensitivity is a major source of error. A shift of only 0.1 pH units produces a 15% relative change in fluorescence, making it impossible to exactly reproduce earlier readings on standards when a new batch of buffer is prepared. False positives are also attributed to the reagent L-leucyl-L-alanine, which can vary considerably from brand to brand and from lot to lot (52). The fluorometric method is expensive and tedious. In addition, antibiotics such as ampicillin have been found to spontaneously fluoresce, preventing accurate diagnosis of infants that may have antibiotics in their serum (50).

Colorimetric Tests including Ferric Chloride Test and 2,4 Dinitrophenylhydrazine Test (DNPH)

The ferric chloride test is an assay that is used to identify a variety of drugs and metabolites in urine by generating various colors. A green color in the ferric chloride test indicates a positive result for PKU. The 2,4-Dinitrophenylhydrazine test is used to confirm a positive result for PKU by the ferric chloride test. 10 minutes after the addition of the DNPH reagent, the appearance of a yellow precipitate indicates the presence of alpha-keto acids.

Although both of these screening tests are sensitive, they are not specific. Positive results in either test must be confirmed by definitive assays for phenylalanine. Also, measurements of metabolites in the urine, such as phenylpyruvic acid, are generally not as reliable as measuring phenylalanine levels in the blood since metabolites may not be present in the urine before 4 to 6 weeks of age.

Chromatography

One dimensional thin-layer chromatography (TLC) is often performed to confirm a positive result from one of the preceding assays. From a urine sample, TLC can identify abnormal amino acid patterns. As many as six urine samples may be assayed on a single plate that includes an amino acid standard. Since the urine of young infants contains higher concentrations of urinary amino acids, pooled infant urine is also used as a control in the effort to avoid false positive results. Two dimensional TLC may also be employed, particularly after a positive result from the one dimensional TLC, as the separation of amino acids is more distinct. In both one and two dimensional chromatography, duplicate plates are made so that one may be stained with ninhydrin and the other with isatin. Isatin enables the identification of proline and hydroxyproline, and produces unique colors for several amino acids, including phenylalanine. It also allows for the identification of interferences such as antibiotics which give a bright yellow color rather than the pink color produced by most amino acids.

Although this assay is used to confirm "positive" colorimetric test results for PKU, it is not definitive. If abnormal results are obtained from two-dimensional chromatography, it is recommended that an HPLC assay be done on a serum or plasma sample to confirm and quantify the abnormal amino acid. In mechanical terms, smaller plates for TLC have shortened the duration of this assay. However, thin-layer chromatography remains a labor intensive and time-consuming process. High-performance liquid chromatography (HPLC) is the gold standard for identifying and quantifying phenylalanine and metabolites in biological fluids. However, the equipment is expensive and the procedure is laborious.

Clearly, there is a need for methods which enable detection of a target in diagnostic enzymatic immunoassays because such methods would provide quick and accurate diagnostic assessment of the presence or absence of a clinically important target molecule, the presence or absence of which can be correlated to a disease state or disorder. The present invention meets that need.

SUMMARY OF THE INVENTION

The invention permits the detection of a target organic molecule through the capacity of the target molecule to regulate an artificial enzyme which acts on a substrate designed to produce an easily detected reporter molecule. The target molecule can be an inhibitor, in which case production of the reporter molecule indicates the absence of the target molecule, or the target molecule can be a cofactor, in which case production of the reporter molecule indicates the presence of the target molecule.

Inhibitor Assay

The present invention, as embodied in the Inhibitor Assay, takes advantage of the heretofore undesirable property of product inhibition, characteristic of many catalytic monoclonal antibodies (also referred to herein as cMabs), thereby providing the basis for a new, general method by which any organic molecule can be identified qualitatively or quantitatively.

The invention utilizes a construction in which any target organic molecule, either directly or with a minor structural modification (such as the attachment of a linker moiety), can be covalently bound to a reporter molecule and this target-reporter molecule can be a substrate of a catalytic antibody; the target organic molecule, as a product (or a molecule closely related to a product) of the antibody-catalyzed cleavage of the substrate molecule, can be a competitive inhibitor of that reaction. This inhibition is termed "product inhibition" if the target organic molecule is identical to one of the products, or, as termed here, "product-related inhibition" if the target resembles but is not identical with the product due to the additional presence of a linker group in that product.

The invention, as embodied in the Inhibitor Assay, provides a method for determining the absence of a target organic molecule in a sample by adding to the sample a substrate which is the conjugate of the target organic molecule attached by a cleavable linker to the reporter molecule such that cleavage of the substrate at the linker produces the reporter molecule.

The method further provides adding a cMab to the sample which binds the target organic molecule and when the target organic molecule is not present in the sample the cMab will bind and cleave the substrate molecule. Finally, the method provides detecting a change in the sample, the change being the production of the reporter molecule by the antibody-catalyzed reaction, thereby signifying the absence of the target organic molecule.

Prior to applicant's invention, catalytic antibodies inactivated by their products had no practical utility. Applicant has discovered that a rationally obtained, product-sensitive artificial enzyme can be used for a specific and sensitive assay of the original target organic molecule (which is either identical to or closely resembling a reaction product of the artificial enzyme). That is, as an illustration, in the presence of this target molecule, the artificial enzyme would be inhibited, and the substrate molecule which is the conjugate of the target molecule and a reporter molecule (e.g., a chromophore) will not be cleaved. In the absence of the target molecule, the fully active artificial enzyme will cleave the colorless substrate molecule, thereby releasing the chromophore reporter molecule. The intensity of color (or magnitude of absorbance) will vary inversely with the concentration of the target molecule and can be used to qualitatively, semi-quantitatively or quantitatively identify the target molecule.

Cofactor Assay

The present invention, as embodied in the cofactor assay, utilizes a construction in which any target organic molecule can be associated with a substrate molecule such that an antibody-catalyzed reaction of the substrate molecule requires the coincident binding of the target molecule by the antibody. The target molecule is essential for reaction and is termed a cofactor.

The invention, as embodied in the cofactor assay, provides a method for determining the presence of a target organic molecule in a sample by adding to the sample a substrate molecule which is a conjugate of a "complementary molecule" (i.e., a molecule with functional groups that complement groups of target molecule through non-covalent binding interactions) attached by a cleavable linker to a reporter molecule such that cleavage of the substrate molecule produces the reporter molecule. The method further provides adding a cMab to the sample which binds both the target organic molecule and the substrate molecule and then cleaves the substrate molecule; but when the target is not present the cMab will not react with the substrate molecule. Finally, the method provides detecting a change in the sample, the change being the production of the reporter molecule by an antibody-catalyzed reaction, thereby signifying the presence of the target organic molecule.

Prior to the applicant's invention only selected species, e.g. metal ions, were considered useful as cofactors in antibody catalysis. I determined that the capacity to function as a cofactor is generally intrinsic to biologically interesting target molecules because they typically possess functional groups for hydrogen bonding or salt bridge formation and these groups can be recruited to participate in the antibody binding and/or the antibody-catalyzed reaction of specially tailored substrate molecules. I discovered that a rationally constructed, target-requiring artificial enzyme (in this case, the cMab is the artificial enzyme) can be used for a specific and sensitive assay of the target molecule. That is, as an illustration, in the absence of the target molecule the artificial enzyme would not bind and react with the colorless substrate molecule. In the presence of target, the substrate molecule is bound and the enzyme reacts with the substrate molecule, thereby producing the chromophore reporter molecule. The intensity of color (or magnitude of absorbance) will vary directly with the concentration of the target molecule and can be used to qualitatively, semi-quantitatively or quantitatively to identify the target molecule.

ADVANTAGES OF THE CLAIMED INVENTION: I have overcome the problems associated with detecting target organic compounds using catalytic antibodies. These problems all relate to the fact that only the rarest target molecules are substrates for useful catalytic antibodies. Our solution relies on two complementary assays in which the target organic molecule is not the substrate molecule but rather acts as either an inhibitor or a cofactor for the antibody-catalyzed reaction of a substrate molecule and thereby regulates production of a reporter molecule. Since in either the Inhibitor Assay or the Cofactor Assay the target molecule regulates an enzyme, the turnover of that enzyme greatly amplifies the signal that follows from target-enzyme binding, or absence of binding, and a sensitive assay of the target molecule results. Since in either the Inhibitor Assay or the Cofactor Assay the interaction of target molecule and catalytic antibody occurs at the antigen binding site of the antibody, the binding of target molecule and antibody is specific and a specific assay of the target molecule results.

Further, the methods of the invention are easily used in kits having the "dipstick" methodology format ( i.e., a dipstick, impregnated with catalytic antibody and substrate, is saturated with a fluid to be tested resulting in a colorimetric endpoint indicating the target's presence or absence).

The "dipstick" format addresses the need for simple assays to detect PKU or chlamydial infections.

BRIEF DESCRIPTION OF THE FIGURES

FIGS. 4 and 5 show illustrative reagents needed to implement the method for the detection of chlamydia.

DETAILED DESCRIPTION OF THE INVENTION

Figure 1:
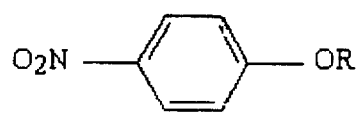
FIG. 1 shows the structures of illustrative reporter molecules.
Figure 1:
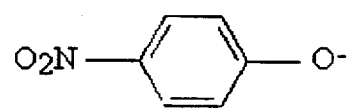
Figure 1:
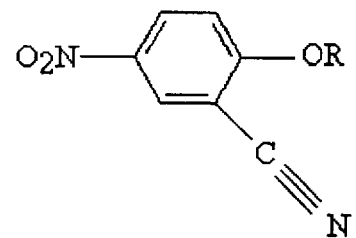
Figure 1:
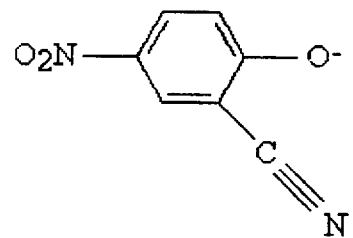
Figure 1:
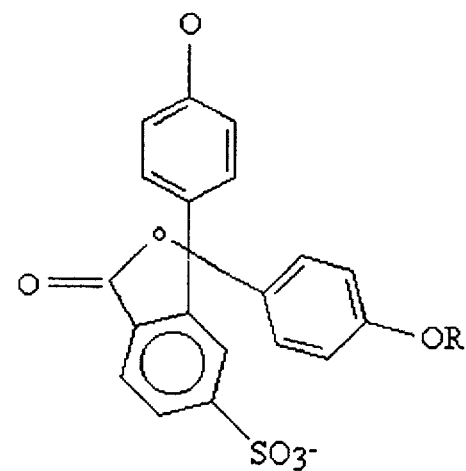
Figure 1:
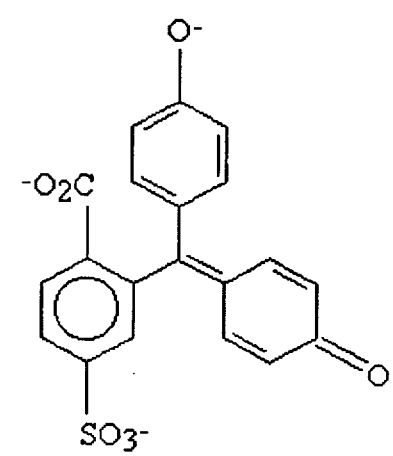
Figure 2:
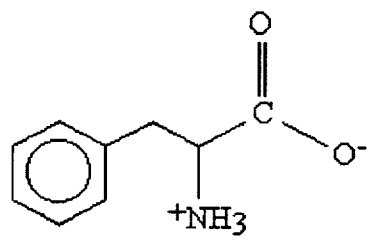
FIGS. 2 and 3 show illustrative reagents needed to implement the method for the detection of phenylalanine.
Figure 2:
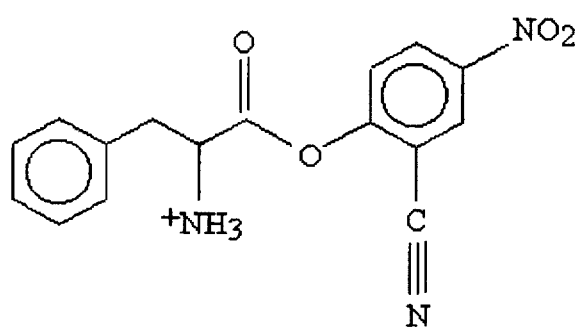
Figure 2:
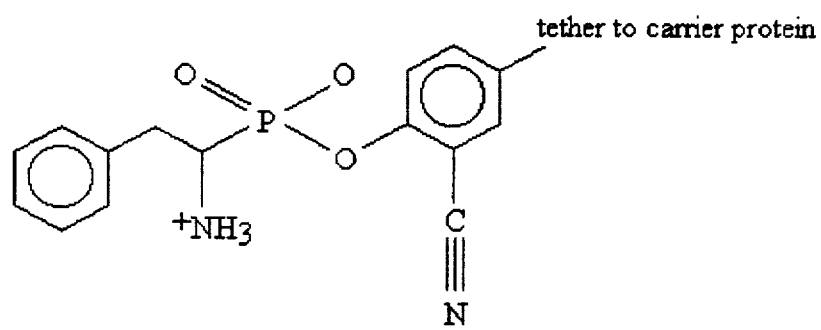
Figure 3:
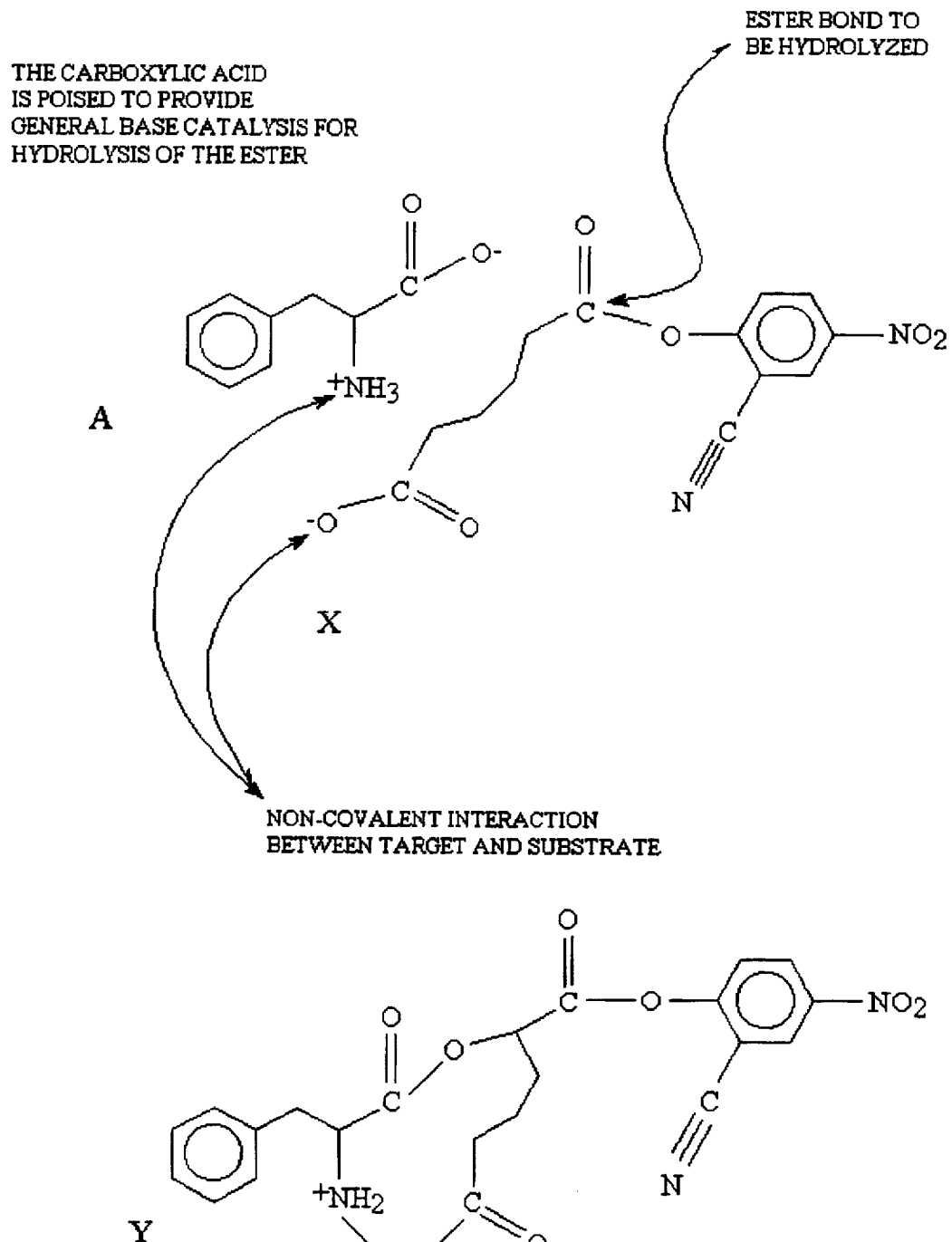
Figure 3:
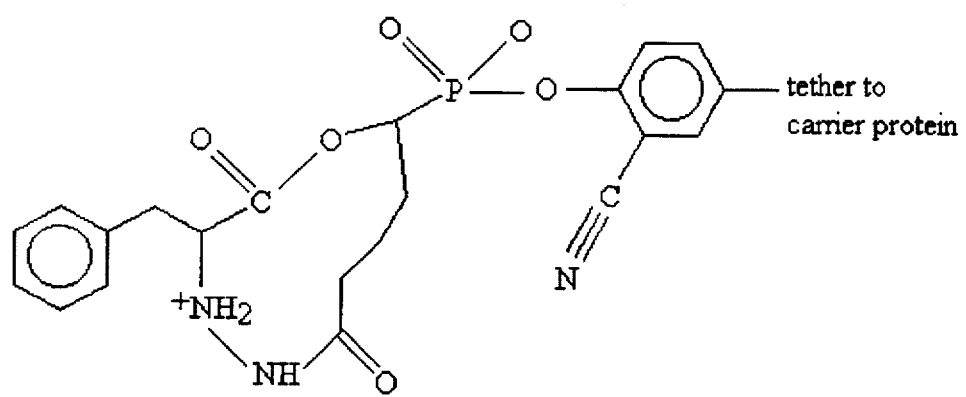

As used in this application, the following words or phrases have the meanings specified.

DEFINITION

As used herein "substrate molecule" means a molecule subject to a reaction catalyzed by an antibody.

As used herein "target molecule" is the organic molecule to be detected.

As used herein "transform" means a covalent modification of the substrate molecule such that the reporter molecule is detectable.

As used herein the term "reporter molecule" means a molecule which is readily detected. Detection may be effected due to properties of color, absorbance, luminescence, fluorescence or phosphorescence.

As used herein "inhibit" means inhibition of any rational sort, e.g., product inhibition.

As used herein "product-related inhibition" means inhibition by a chemical structure differing from the product of the reaction only by the addition of a linker group (e.g., —COOH).

As used herein "Inhibitor Assay" means an assay for the absence of a target molecule based on the capacity of the target to be an inhibitor of an antibody-catalyzed reaction.

As used herein "Cofactor Assay" means an assay for the presence of a target molecule based on the capacity of the target to be a cofactor of an antibody-catalyzed reaction.

As used herein "activated ester" refers to the readily cleaved ester of a carboxylic acid and the hydroxyl derivative of an aromatic species such as a phenol or a hydroxycoumarin derivative.

As used herein "complementary" means possessing functional groups (e.g. —COOH, —NH$_2$, —OH) spatially arranged to bind non-covalently one or more corresponding groups of another molecule As used herein "target-substrate molecule" means a chemical structure in which a target molecule is covalently bound to a substrate molecule in a fashion that preserves the orientation of atoms anticipated in the non-covalent interaction of the target molecule and the complementary portion of the substrate molecule.

As used herein "positive" results refers to a result that indicates or implies the presence of the target molecule, e.g., no production of reporter molecule in the Inhibitor assay or the production of reporter molecule in the Cofactor Assay.

In order that the invention herein described may be more fully understood, the following description is set forth.

INHIBITOR ASSAY

The present invention, as embodied in the Inhibitor Assay, provides a method for determining the presence or absence of a target organic molecule in a sample. The method comprises obtaining the sample to which sample a substrate molecule is added. The method further comprises adding a cMab to the sample which recognizes either the target organic molecule in the sample or the substrate molecule, but preferentially binds the target organic molecule when both are present in the sample. When the target molecule is not present in the sample the cMab binds exclusively to the substrate molecule. This binding and reaction of substrate molecule creates a detectable change which signifies the absence of the target organic molecule.

The substrate is a variant of the target organic molecule, i.e., it is the target organic molecule covalently linked to a reporter molecule. The substrate molecule competes with the target molecule for cMab binding in the sample when the target molecule is present or the substrate molecule binds the cMab when the target molecule is absent. The binding of substrate molecule to cMab is detected by production of the reporter molecule.

The cMab recognizes and binds the target organic molecule when the target organic molecule is present in the sample; or recognizes and binds the substrate molecular when the target organic molecule is not present in the sample.

The detectable change in the sample is the product of an antibody-catalyzed reaction of the substrate molecule, i.e., the release of the reporter molecule from the substrate molecule. When the change is detected then the target molecule is not in the sample. The catalytic monoclonal antibody has a sufficient affinity for the target molecule compared to the substrate molecule that, in the concentration range of target to be deemed a positive result and at the concentration of substrate molecule employed, antibody binds target preferentially compared to substrate molecule.

In typical practice, the substrate molecule is present at a concentration near to or less than the Km of the catalytic antibody; the lowest concentration of target to be deemed a positive result is near to or greater than the $K_i$ of the target molecule for the catalytic antibody. When the target molecule is not present the cMab can only bind the substrate molecule added to the sample and, therefore, the change determines the absence of an organic molecule in a sample. No detectable change in the sample signifies the presence of the target molecule in the sample and constitutes a "positive" test for the target molecule.

Ester hydrolysis, in a preferred practice of the present invention, is one of the chemical reactions by which a catalytic antibody produces the reporter molecule and, for simplicity, will be the focus of the following explanation. Nonetheless, a variety of other reactions are useful including hydrolysis of carbonates and elimination of quaternary amines (53–55).

A target molecule is chromatographically purified as necessary for 99+% purity and, if containing a carboxylic acid group, then directly coupled to the hydroxyl group of a reporter molecule by means of standard methods for the synthesis of esters, e.g. dicyclohexylcarbodiimide coupling, to yield the substrate molecule. If a target molecule does not contain a carboxylic acid group then a derivative of the target molecule containing a carboxylic acid group is synthesized.

If a target molecule contains a simple carboxylic amide or ester then hydrolysis of the carboxylic group easily provides the free carboxylic acid. If neither a carboxylic acid, an ester or an amide is present in a target molecule then the target molecule is synthesized de novo to contain a carboxylic acid group positioned away from other functional groups of the target molecule. The target molecule, chemically modified as above, is then coupled via an ester linkage to the hydroxyl group of a reporter molecule to yield the substrate molecule.

The reporter molecule has a hydroxyl group for coupling by an ester linkage to the carboxylic acid of target molecule, or target molecule modified as above to contain a carboxylic acid. The reporter molecule has the property of changing color, absorbance, luminescence, fluorescence or phosphorescence when released by cleavage of the ester linkage.

The reporter molecule in a preferred embodiment is a molecule having the property of changing color and/or absorbance when an ester linkage to the reporter molecule is cleaved. Cleavage of the ester linkage to the reporter molecule frees a hydroxyl group of the reporter molecule; the hydroxyl group of the reporter molecule has the property of being ionized at the pH of the assay (typically pH 7 to pH 10). Ionization of the hydroxyl group of the reporter molecule results in an increase in absorbance and a shift in the lambda max associated with the development of color or a change in color detected visually or by means of a spectrophotometer. This property of changing color depending on ionization state is simply the property of being a pH indicator and pH indicator molecules, when incorporated into an enzyme substrate molecule and released by enzymatic reaction, are well known as reporter molecules (56–58) In this manner, hydrolysis of the ester linkage of the substrate molecule produces the reporter molecule, i.e., the reporter hydroxyl group is no longer incorporated in an ester and the released reporter molecule changes color.

Hydrolysis of the ester refers to cleaving the ester linkage of the substrate molecule with the introduction of a molecule of water to release the hydroxyl-containing reporter molecule.

The ester of a reporter molecule based on a pH indicator dye is an "activated" ester—i.e., an ester of an aromatic hydroxyl-containing molecule. The hydroxyl group of such a reporter molecule has a low pKa (pKa<12) and hydrolysis of an ester of such a reporter is facile and antibody-catalyzed hydrolysis of these esters tends to occur at higher rates.

Catalytic monoclonal antibodies with the desired properties are made and identified by standard methods as follows (13,17,26). A transition-state analog of the substrate molecule is constructed which varies from the structure of the substrate molecule in two ways (i) the ester linkage between target molecule and reporter is replaced by a phosphonate monoester, and (ii) the reporter molecule is modified to include a tether for the preparation of an immunogenic conjugate to carrier protein (e.g. keyhole limpet hemocyanin or bovine serum albumin).

Generally, mice are immunized by standard protocols and immune responders are identified by ELISA of mouse plasma tested against the transition-state analog coupled to a protein (e.g. ovalbumin) different from the immunogenic carrier protein (59).

The spleens of the responders are harvested and fused with NS. 1 cells to yield hybridomas. Hybridoma media supernatant is screened by ELISA to identify producers of anti-transition-state analog antibodies. The antibodies are then incubated with the substrate molecule and observed. A color change, expected for the production of reporter molecule, indicates the presence of active cMab. The active cMab's are then screened for the property of inhibition by target molecule in the concentration range of target molecule intended for a positive result.

In an alternative standard method for obtaining catalytic antibodies, transition-state analog may be attached by its tether to a column support and used to screen phage displaying a combinatorial library of immunoglobulin Fab fragments (60–62). The phage selected for the property of binding the transition-state analog are eluted and the Fab fragments are expressed in *E. coli*. Fab fragments, as for whole antibodies above, are incubated with the substrate molecule and observed. A color change expected for the production of reporter molecule, indicates the presence of active enzyme. The active Fab's are screened for inhibition by target molecule in the concentration range for target molecule desired for the assay. Such inhibition has previously been an impediment to the useful application of catalytic antibodies but now becomes an essential characteristic.

A single catalytic antibody with a K of inhibition by the target molecule $K_i$(target molecule) of lower magnitude than the lowest concentration of target molecule intended for a positive assay result, is preferable for these assays. Alternatively, since several enzymes with a range of values for $K_i$(target molecule) will be identified by random screening of active cMabs, a panel of enzymes with $K_i$'s varying across the potential concentration range of the target molecule could be used in the construction of a very sensitive quantitative assay.

Although one of the products from hydrolysis of the substrate molecule, i.e. the carboxylic acid-containing target molecule, is itself an inhibitor of the catalytic antibody, the concentration of this product and, therefore, that of the reporter molecule must rise before inhibition can occur. The production of a reporter molecule indicate the absence of target molecule in the original sample. Nonetheless, to further enhance the sensitivity of the assay, the substrate molecule (in the preferred embodiment, an activated ester) may be modified to differ slightly in chemical structure from the structure upon which the transition-state analog immunogen was based such that:

(1) the binding of the catalytic antibody to the substrate molecule is weakened (Km is increased) relative to its binding to the sample's inhibitory target molecule ($K_i$ is relative low); and (2) the products released by hydrolysis of the substrate molecule will not themselves display excessive product inhibition.

The range of modification in the substrate molecule to optimize $K_i$ vs Km is small (e.g. replacement of a methyl group with an ethyl, or a chloride with a bromide in the position of the substrate molecule corresponding to the target molecule) since more comprehensive changes result in a rejection of the modified substrate molecule by the artificial enzyme.

| Schematic for Inhibitor Assay: | |
|---|---|
| 1. Urine with "A." | 1. Urine without "A." |
| 2. Add cMab. | 2. Add cMab. |
| 3. Add "A-COO-Reporter" | 3. Add "A-COO-Reporter" |
| Positive test for "A" | Negative test for "A" |
| Remains colorless since A inhibits cMab | Turns blue as cMAb cleaves "A-COO-Reporter" and releases Reporter |

COFACTOR ASSAY

Additionally, the present invention provides a method for determining the presence of a target molecule organic molecule in a sample (e.g. the Cofactor Assay). The method comprises obtaining the sample, to which sample a substrate molecule is added. The method further comprises adding a catalytic monoclonal antibody to the sample which does not catalyze the reaction of the substrate molecule in the absence of target molecule but in the presence of the target molecule the cMab binds both target molecule and substrate molecule thereby catalyzing the reaction of the substrate molecule to produce the reporter molecule, the production of the reporter molecule being indicative of the presence of the target molecule organic molecule in the sample.

The cMab recognizes and binds the target organic molecule and the substrate molecule and catalyzes a chemical reaction of the substrate molecule when the target organic molecule is present in the sample; and fails to recognize and bind and/or fails to catalyze the chemical reaction of the substrate molecule when the target organic molecule is not present in the sample.

The detectable change in the sample is the product of an antibody-catalyzed reaction of the substrate molecule, i.e., the release of the reporter molecule from the substrate molecule. The detectable change in the sample signifies that the target molecule is present in the sample and constitutes a "positive" test for the target molecule.

The substrate molecule is the conjugate of (1) a "complementary molecule" containing functional groups for non-covalent binding to corresponding functional groups of the target molecule and (ii) a reporter molecule such that an antibody-catalyzed reaction of the substrate molecule produces the reporter molecule. The antibody binds the target molecule and orients functional groups of the target molecule to participate in the binding and/or catalysis of substrate molecule and the target molecule thus functions as a cofactor for the production of reporter.

An artificial enzyme that recruits a functional group, not part of the enzyme itself, to participate in the catalytic transformation of a substrate molecule has precedent in the phenomenon of substrate-assisted enzyme catalysis. For example, a peptidase was modified by removal of a key catalytic amino acid through site-directed mutagenesis and, as expected, the enzyme lost activity. However, activity was restored after the missing amino acid was placed within the peptide substrate molecule (63). Another precedent is found in the generation of antibodies that catalyze the hydrolysis of an ester or amide linkage by means of a metal cofactor (64). These hydrolytic artificial enzymes were obtained by immunizing with a transition-state analog that incorporated a metal ion. The antibodies elicited by this analog possessed a binding site for the free metal as well as a binding site for the substrate molecule and, for some of these antibodies, hydrolysis of the substrate molecule required the free metal i.e., the metal was a necessary cofactor.

I determined that the capacity to function as a cofactor is a general one for molecules with functional groups suitable for hydrogen bonding and salt-bridge formation—the sort of groups present on the vast majority of clinically important target molecules. For any given target, a substrate molecule can be designed that complements functional groups of the target molecule to permit hydrogen bounding or salt bridge formation and this complementary molecule can be linked to a reporter molecule to yield the substrate molecule. Immunization with the substrate molecule's transition-state analog—to which analog is covalently attached the target molecule—can give rise to antibodies that require target molecule for the proper binding and reaction of substrate molecule. The target molecule is incorporated into the analog in a manner so as to mimic the atomic configuration of the non-covalent interaction of target molecule and substrate molecule, and the resulting catalytic antibody has a binding pocket that can simultaneously accommodate both target molecule and substrate molecule. The binding pocket elicited by such an analog orients the target molecule to participate in substrate molecule binding and/or catalysis. The result is an artificial enzyme which requires target molecule as a cofactor for reaction.

In practice, a covalently linked version of the interaction of target molecule and substrate molecule interaction (i.e., a target-substrate molecule that maintains the geometry of the non-covalent interaction of target molecule and substrate molecule) is synthesized and serves as a screening substrate molecule for the desired artificial enzyme. The substrate molecule portion of this target-substrate molecule contains the site for antibody-catalyzed reaction, and this site is the cleavable linkage by which the reporter molecule is incorporated into the substrate molecule.

In a preferred embodiment, the target molecule will non-covalently bond with the substrate molecule in such a fashion that this binding will stabilize the transition-state for substrate hydrolysis and/or participate in covalent or acid-base catalysis and thus participate in the catalytic release of reporter molecule.

To obtain a cMab with the desired property of cofactor dependence, a transition-state analog of this target-substrate molecule is synthesized by standard methods, e.g., if the substrate molecule contains a reporter moiety bound through an ester group, then the transition-state analog to be synthesized could correspond to the target-substrate molecule modified as follows:

(1) replacement of the carboxylic acid ester with a phosphonate monoester and, (2) attachment of a tether from the substrate molecule portion of the analog to facilitate preparation of an immunogenic conjugate.

Employing known methods, immunization of mice or screening of a phage display system with the transition-state analog of the target-substrate molecule yields analog-binding monoclonal antibodies (whole antibodies or Fab fragments). The anti-analog Mab's are screened for the capacity to hydrolyze the target-substrate molecule. The catalytic cMabs are then screened for the capacity to hydrolyze the free substrate molecule if and only if the free target molecule is present in the sample.

An antibody with these properties can transform the substrate molecule to release the reporter molecule if and only if the target molecule is present as a cofactor with the detection of reporter molecule indicating the presence of target molecule.

| Schematic for Cofactor Assay | | | |
|---|---|---|---|
| 1. | Urine with "A" | 1. | Urine without "A" |
| 2. | Add cMab | 2. | Add cMab |
| 3. | Add "B-COO-Reporter" | 3. | Add "B-COO-Reporter" |
| Positive test for "A": | | Negative test for "A" | |
| Turns blue as cMab binds molecule, cleaves "B-COO-Reporter" and releases Reporter | | Remains colorless since in the target absence of A, cMab does not cleave "B-COO-Reporter" | |

FURTHER ASPECTS OF THE INVENTION

The present invention embodied in the Inhibitor Assay or the Cofactor Assay also provides a method for diagnosing in a subject a disease condition associated with the presence of a target organic molecule which comprises determining in a sample from the subject the presence of the target organic molecule in accordance with the present method, the presence of the target organic molecule indicating the presence of the disease condition.

Further, the present invention provides a method for monitoring the course of a disease condition in a subject which comprises determining in a first sample from the subject the presence of a target organic molecule according to a method of the invention and comparing the amount so determined with the mount present in a second sample from the subject, such samples being taken at different points in time, a difference in the amounts determined being indicative of the course of the disease condition.

The present invention provides a method for detecting the presence of a drug in samples from a subject. The drug may be a substance of abuse, a pharmaceutical agent, or a poison.

In an alternative embodiment, the method of the invention can monitor changes in the concentration of a drug in a subject. This is important in clinical situations where treatment of a condition involves use of a drug having a narrow therapeutic index. Below the therapeutic index, the drug is impotent in vivo. Beyond the therapeutic index, the drug provides a toxic detrimental effect in vivo.

The appropriate ranges for using catalytic monoclonal antibodies and substrate molecules in accordance with the methods of the invention depend upon the type of assay used. Appropriate ranges will vary depending on the amount of the sample and target molecule. Approximate ranges include one nanomole to one millimole.

In accordance with the methods of the invention, the target molecule may be, but is not limited to, phenylalanine. Further, the sample may be, but is not limited to, a cell sample, a tissue sample, a biological fluid sample. Non-clinical samples can include soil, water, industrial or forensic samples.

In accordance with the practice of the invention, the subject may be a human subject, or an animal subject, such as a dog, horse, cat, cow, pig.

The sample of target molecule may be obtained by any known method including for clinical specimens: surgical biopsy, needle biopsy, venipuncture, lumbar puncture, paracentesis, thoracentesis, joint aspirate, gastric aspirate, urine sampling, and stool sampling, In accordance with the present invention, the substrate molecule upon antibody-catalyzed reaction produces a detectable marker such as a radioactive label ($^{125}$I), a colorimetric marker, a fluorometric marker, a phosphorescent marker, a luminescent marker, or a participant in a second enzymatic reaction.

The catalytic monoclonal antibody may be bound to a matrix such as agarose or sepharose. Alternatively, the catalytic monoclonal antibody is bound to a tube. Further, alternatively, the catalytic monoclonal antibody is bound to a bead.

In the detection step, the change can be a visual change such as a change in the color of the sample. Alternatively, the change can include any difference or variation that is measurable. Preferably, the change is the product of an antibody-catalyzed hydrolysis reaction. It is the determination of this change which allows those skilled in the art to determine the presence or absence of the target molecule in a sample.

Disease conditions include metabolic disorders such as PKU and infections such as *Chlamydia trachomatis*.

Drugs to be detected include substances of abuse such as heroin, cocaine or barbiturates, pharmaceutical agents requiring monitoring in order to achieve a therapeutic level or avoid a toxic level such as digoxin, vancomycin, or theophylline; poisons such as insecticide principals.

EXAMPLE 1

The following protocol teaches how to make reagents for the practice of the Inhibitor Assay, a method for determining the absence of a target organic molecule (designated "Target molecule"). The "Target molecule" can be any clinically important organic molecule. The substrate molecule for this example is presumed to be an ester.

Method:

Synthesize an analog of "Target molecule" with an appended "—COOH" or other point of attachment, if it is not already present in the molecule. The attachment of a carboxylic acid group in place of a hydrogen is accomplished by standard methods that vary with the chemical structure of the target molecule (65). Assume "COOH" is added to the target molecule for this example to yield "Target molecule-COOH."

Synthesize a substrate molecule "Target molecule-COO-Reporter" where the substrate molecule has one property (e.g. absence of color), but the cleavage product "Reporter" has another or a modified property (e.g., new color or different color). The carboxylic acid (Target molecule-COOH) is activated by an appropriate method, e.g. $SOCl_2$. To this activated acid is added the hydroxyl-containing reporter molecule, e.g. 2-cyano-4-nitrophenol, in a minimum amount of reaction solvent. After an appropriate interval the solvent is evaporated at reduced pressure and the residue purified by column chromatography to yield the "Target molecule-COO-reporter."

Synthesize a phosphonate monoester immunogen "Target molecule-POO-Reporter-carrier protein," generate antibodies to this immunogen, and screen for catalytic monoclonal antibodies (cMab) that will hydrolyze "Target molecule-COO-Reporter". The design and synthesis of transition-state analogs are well known both in general (13–27,66) and in particular for the hydrolysis of esters (13,17,26,67) and relies on substituting a phosphonate monoester "POO-R" for the carboxylic acid ester "COO-R moiety."

Generate cMab's by standard methods. The methodology for immunizing mice or screening phage to generate monoclonal immunoglobulin and for screening these immunoglobulin for cMab activity is also well known (56). To screen Mab's for cMab activity, incubate the Mab (1 µmolar) with 1–1000 µmolar substrate molecule in a phosphate buffer pH 7–9. Production of reporter, in excess of that produced in a control reaction without cMab, indicates the presence of a reaction catalyzed by a cMab. Inhibition of cMab activity by T-POO-Reporter (free transition-state analog) confirms the presence of an artificial enzyme.

Screen the cMab's for those displaying inhibition by target molecule—a molecule identical to or very similar in structure to a product of the reaction. Product inhibition is a well known and previously undesirable property of some catalytic antibodies.

To screen cMab's for inhibition by target molecule (i) incubate cMab (1 µmolar) with target molecule at a concentration equal to the minimum concentration to be discriminated by the test (ii) add substrate molecule (iii) observe for absence of reporter relative to a control with cMab and substrate molecule but not target molecule; absence of reporter indicating inhibition by target molecule, (iv) determine Ki of target molecule by standard protocols (64–66).

Continue screening until a cmAb is found with a $K_i$ near or below the desired limit of detection for target molecule (e.g. a $K_i$ of 10 µM is satisfactory if the minimum concentration to be discriminated by the test is a target molecule concentration of 100 µM).

EXAMPLE 2

The following protocol teaches how to make reagents for the practice of the Cofactor Assay method, a method for determining the presence of a target organic molecule in a sample. The assay comprises the use of a substrate molecule having the following characteristics: (i) a non-covalent binding domain which is complementary to the target molecule and (ii) a reporter domain that is detectable when transformed by an antibody-catalyzed reaction, and comprises the use a cMab with the capacity to cleave the substrate molecule if and only if the cMab has also bound the target molecule.

Construct the substrate molecule as an ester molecule that complements the "Target-COO-Reporter" of a hydroxyl-containing reporter molecule and a carboxylic acid whose functional groups complement and bind one or more functional groups of the target molecule by hydrogen bonding or salt-bridge formation. The general protocol including the synthesis of the carboxylic acid moiety of the substrate molecule tailored to the particular target molecule, is performed by standard methods. The hydroxyl-containing portion in a preferred embodiment is an aromatic hydroxyl compound having the property described above of changing color and absorbance upon changing ionization state.

Construct target-substrate molecule "Target molecule-molecule that complements the Target-COO-Reporter" in which the non-covalent interactions between target molecule and substrate molecule are replaced by covalent linkage(s). The target-substrate molecule is designed to maintain the distances and geometry of the major (non-hydrogen) atoms in the non-covalent interaction expected for target molecule and substrate molecule. As examples, the hydrogen bonding interaction $R—CH_2—O—H \ldots NH_2—R$ is replaced by the species $R—CH_2—NH—NHR$ or $R—CH_2O—NH_2—R$; and the salt bridge $R—C(O)O^- \ldots H_3N^+—R$ is replaced by $R—C(O)NH—N^+H_2—R$.

Synthesize a transition-state analog of the target-substrate molecule with a phosphonate monoester replacing the carboxylic acid ester and with a tether to carrier protein to yield "Target molecule-molecule that complements the Target-POO-Reporter-Carrier Protein", generate antibodies to this immunogen, and screen for catalytic monoclonal antibodies (cMab) that will hydrolyze the ester linking molecule that complements the Target and "Reporter" in the target-substrate molecule to yield the reporter molecule. The design and synthesis of transition-state analogs is well known both in general and in particular for the hydrolysis of esters. The methodology for immunizing mice or screening phage to generate monoclonal immunoglobulin and for screening these immunoglobulin for cMab activity is also well known. To screen Mab's for cMab activity, incubate the Mab (1 μM) with 1–1000 μM substrate molecule-target molecule in a phosphate buffer pH 7–9. Production of reporter, in excess of that produced in a control reaction without Mab, indicates the presence of a cMab.

Screen the cMabs, identified as above to be active against the covalently linked target-substrate molecule, for hydrolytic activity against the free substrate molecule in the presence or in the absence of free target molecule. Incubate cMab (1 μM) with substrate molecule (1–1000 μM) in phosphate buffered saline in the presence or absence of target molecule at a concentration equal to the desired limit of detection. The desired antibodies are those which hydrolyze the substrate molecule if and only if the target molecule is present. The Km of the enzyme is determined by standard methods (71, 72). The ideal cMab will have a Km (in the condition of substrate molecule excess) near or below the desired limit of detection for the target molecule.

EXAMPLES 3A AND B

Catalytic Antibody-Based Assay For Phenylalanine

Based on the previous discussion, a simple assay for the plasma constituent phenylalanine is specified below. The assay is configured to provide a colorimetric endpoint based on target molecule inhibition or target molecule enhancement (cofactor effect) of a reaction that activates a latent chromophore by means of the antibody-catalyzed production of a reporter molecule. Since phenylalanine contains a carboxylic acid group, no modification is required in order to attach this target molecule via an ester linkage to a reporter molecule (example 3A) and the functional groups of phenylalanine permit construction of a complementary substrate molecule (example 3B).

3A. Inhibition. Assay (FIG. 2):

1. Designation of target molecule:
   Phenylalanine is the target molecule structure A.
2. Synthesis of substrate molecule:
   The carboxylic acid group of phenylalanine is transformed to an ester linking the target molecule to a reporter molecule to provide the substrate molecule B. In this instance the reporter molecule is a chromophore.
3. Synthesis of transition-state analog and generation of catalytic antibodies:
   A phosphonate ester C is synthesized as a transition-state analog for the carboxylic ester linking the target molecule carbonyl to the reporter molecule.
4. Screen for catalytic antibodies:
   Monoclonal antibodies generated against C are screened for catalytic activity against the substrate molecule B.
5. Screen for product-analog inhibition:
   Catalytic monoclonal antibodies active against the substrate molecule B are screened for susceptibility to inhibition by the target molecule A in the diagnostic concentration cut-off range of 0.4–0.6 mM.

3B. Cofactor Assay (FIG. 3):

1. Target molecule designation:
   As above, the analyte phenylalanine is the target molecule structure A.
2. Design of target molecule-substrate molecule interaction:
   The charged ammonium group of phenylalanine provides a site for electrostatic interaction between target molecule A and a complementary substrate molecule X. The substrate molecule has a complementary binding domain connected by an ester linkage to a reporter molecule.
3. Synthesis of covalent version of target molecule-substrate molecule interaction:
   The interaction of the carboxylate group of X and the ammonium of A can be mimicked by a covalently bound species Y that retains the spacial orientation of the major (non-hydrogen) atoms.

4. Synthesis of the transition-state analog:
   A transition-state analog of Y is constructed with a phosphonate monoester in place of the carboxylic acid ester attached to the reporter molecule to yield Z.

5. Screen for target molecule dependent cMab hydrolysis of substrate molecule:
   Monoclonal antibodies to Z are screened for those which hydrolyze Y and those catalytic antibodies that hydrolyze Y are screened for those that hydrolyze X only if A is present in the diagnostic concentration range of 0.4–0.6 mM.

EXAMPLES 4A and 4B

Catalytic Antibody-Based Assay for the major outer membrane protein (MOMP) of *Chlamydia trachomatis*

MOMPs appear to modulate the critical events of attachment, induction of phagocytosis, inhibition of phagolysosomal fusion, infectivity, toxicity, and the activity of host immune responses that contribute to immunity and pathogenesis (73). This 40 kD surface-exposed integral membrane protein accounts for more than 60% of the total cell wall protein. MOMP is also the primary serotyping antigen of *Chlamydia trachomatis* isolates (39,40). To date, 15 serovars of *Chlamydia trachomatis* have been identified. Serovars A, B, Ba, and C are the etiological agents of trachoma, serovars D–K are the primary cause of oculogenital infections, and serovars L1, L2 and L3 principally produce lymphogranuloma venereum (74). A useful assay should detect at least the oculogenital-associated serovars and preferably all 15 serovars pathogenic in man.

Comparative analysis of amino acid sequences of different serovars demonstrate that the MOMP genes encode for a highly conserved protein structure. This structure is characterized by four evenly spaced domains, portions of which sequences vary among the different serovars. The locations of these Variable Domains of the MOMP amino acid sequences are VD I (aa 64–83), VD II (aa 139–160), VD III (aa 224–137) and VD IV (aa 288–317). VD I, VD II, and VD IV have contiguous antigenic determinants that elicit the formation of either serovar-, subspecies-, serogroup- or species-specific antibodies. They protrude toward the external environment, as shown by their susceptibility to cleavage by trypsin and accessibility to antibody binding. VD I and VD II show the greatest amount of interserogroup sequence variation, and are the locations of serovar-specific determinants. VD IV, located by the C-terminus of the protein, is the largest of the domains and is species specific (66).

On the basis of sequence analysis of MOMP mRNA, VD IV region can be divided into 3 different sub-domains. The N-terminal region of VD IV (an 288–295), is charged and weakly hydrophilic. The C-terminal region (an 307–317), is both highly charged and hydrophilic, except in serovars F and G. The central region of VD IV (aa 296–306), is uncharged, strongly hydrophobic, and highly conserved. A nine amino acid sequence TTLNPTIAG, (an 298–306) is found in all serovars except K, which contains a threonine instead of an alanine at residue 305. The central sequence TTLNPTI in VD4 is present in all 15 serovars making it an excellent target molecule for an assay (75–76).

Monoclonal antibodies were made to this region of the VD IV and screened by ELISA, using whole elementary body as the coating antigen. The species-specific epitope was localized by monoclonal antibody 6E, which reacted strongly with the peptide LNPTIA (an 300–305). The subspecies-specific epitope was identified by monoclonal antibody 10Eii, which was found to bind to the sequence IFDT (an 294–297) (77). The two threonine residues (IFDTTTLNPTIA) have been proposed to be inaccessible at the surface of viable chlamydia, since their presence is not required for antibody binding. In another study, monoclonal antibody CT 47 was raised against a 16 amino acid peptide which encompassed the same subspecies/species region. It was found to be unreactive to hexapeptides TAIFDT (aa 292–297) and AIFDTT (aa 293–298), but bound to IFDTTT (aa 294–299), serovar C, L1 and elementary bodies of 14 different serovars of *Chlamydia trachomatis*. CT 47 not only demonstrated high affinity for the paratope, but a broadening of serological specificity, primarily attributed a reduction of conformational strain in comparison to its counterpart raised against the natural protein (78).

Further proof has since been offered by the use of the overlapping peptide technique. In this study, it was determined that three other monoclonal antibodies, E4, L1-4 or L1-24, which were raised against MOMP, demonstrated reactivity to VD IV. While each had different recognition patterns, all strongly bound to peptides TLNPTI and LNPTIA from the species-conserved region. Additionally, monoclonal antibody E4 recognized SATAIF, previously determined to be a subspecies epitope. In competitive inhibition assays, only E4 could be inhibited by ATAIFDTTTLNPTIAG and FDTTTLNPTIAG. L1-4 or L1-24 neutralizing activity could not be blocked.

Based on the previous discussion, assays for chlamydia can be envisioned based on MOMP inhibition of an antibody-catalyzed reaction or MOMP activation as a cofactor of an antibody-catalyzed reaction.

The following are assays to detect the MOMP in a cell sample.

4A. Inhibition Assay (FIG. 4)

1. Designation of target molecule sequence:
   MOMP is the best target molecule for a specific assay. The assay is constructed from a MOMP fragment AA: a 9 amino acid sequence TTLNPTIAG (aa 298–306) which is species-specific, exposed, accessible and antigenic. The asparagine (aa 301) provides a convenient locus for elaboration to a catalytic antibody.
2. Synthesis of substrate molecule:
   The terminal carbonyl of asparagine-301 is transformed to an ester linking the asparagine carbon framework to a reporter molecule to yield substrate molecule. In this instance the reporter is a latent chromophore BB.
3. Synthesis of transition-state analog:
   A phosphonate ester group functions as a transition-state analog for the carboxylic ester linking the terminal asparagine carbonyl to the label CC.
4. Screen for catalytic antibodies:
   Monoclonal antibodies generated against the analog CC are screened for catalytic activity against the substrate molecule BB.
5. Screen for product inhibition:
   Catalytic monoclonal antibodies active against the substrate molecule BB are screened for susceptibility to inhibition by the target molecule sequence AA and MOMP itself.

Figure 5:
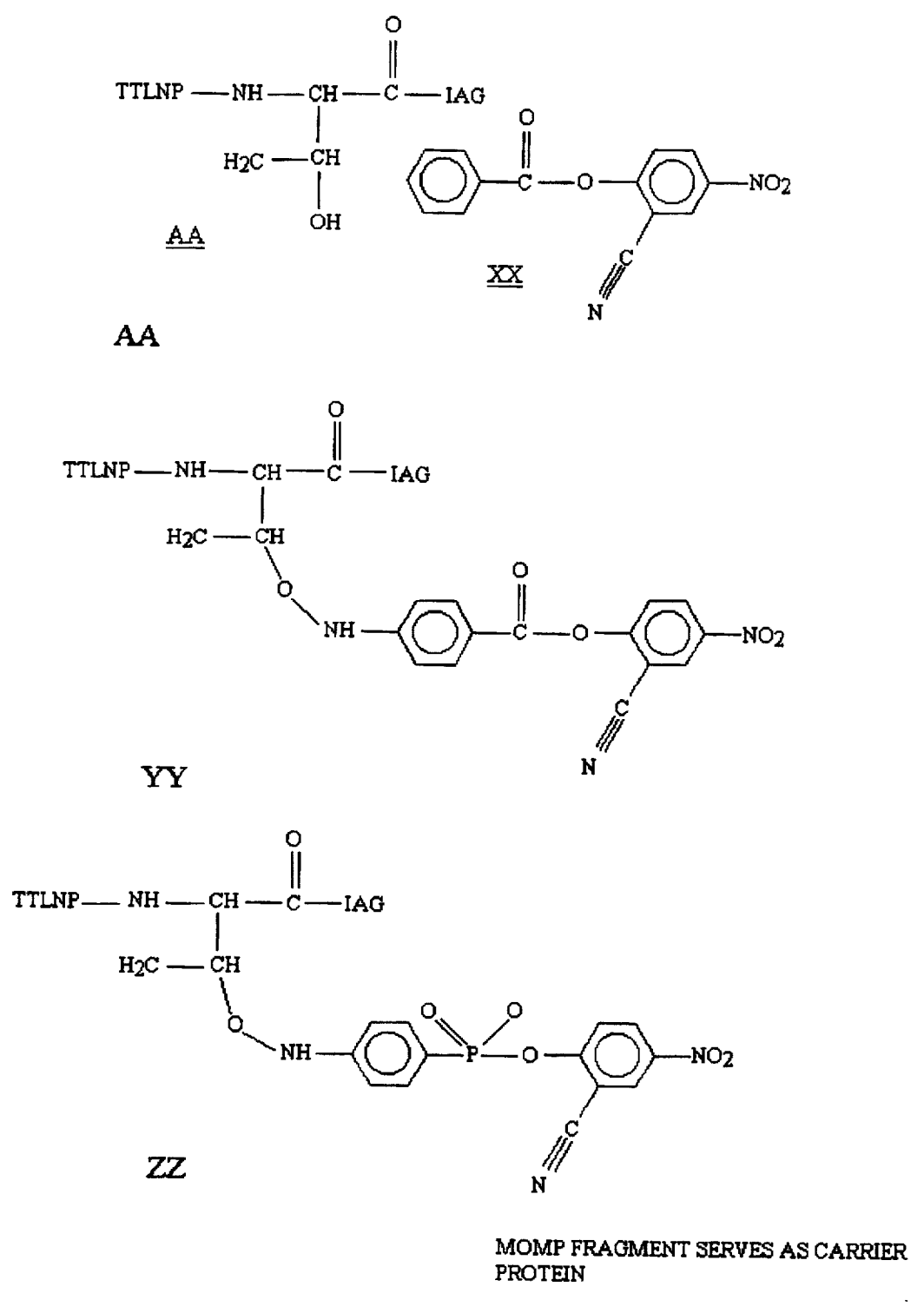

4B. Cofactor Assay (FIG. 5)

1. Designation of target molecule sequence:
   As above, MOMP (specifically the sequence from aa 298–306) is the preferred target molecule and the peptide AA is suitable for assay development.
2. Design of target molecule-substrate molecule interaction:
   The threonine at position 303 of AA provides a site for hydrogen bonding to a complementary substrate molecule XX. The substrate molecule has a complementary binding domain connected by an ester linkage to a reporter molecule.
3. Synthesis of a covalent version of the target molecule-substrate molecule interaction:
   The interaction of the threonine of AA and the binding site of XX can be mimicked by a covalently bound species YY that retains the spacial orientation of the major (non-hydrogen) atoms.
4. Synthesis of the transition-state analog:
   A transition-state analog of YY is constructed with a phosphonate monoester in place of the carboxylic acid ester attached to the reporter molecule to yield ZZ.
5. Screen for target molecule dependent cMab hydrolysis of substrate molecule:
   Monoclonal antibodies to ZZ are screened for those which hydrolyze YY and those that hydrolyze YY are screened for those that hydrolyze XX if and only if AA is present.

EXAMPLES 5A AND 5B

Catalytic Antibody Based Assay for Benzoyl-ecgonine

Simple methods for qualitative or quantitative assay of drugs in biological samples is lacking. The following example illustrates the construction of a simple assay for a metabolite of cocaine, benzoyl ecgonine, that is used to assess recent cocaine exposure. Since benzoyl ecgonine contains a carboxylic acid group, no modification is required in order to attach this target molecule to a reporter molecule (example 5A) or construct a complementary substrate molecule (example 5B).

Figure 6:
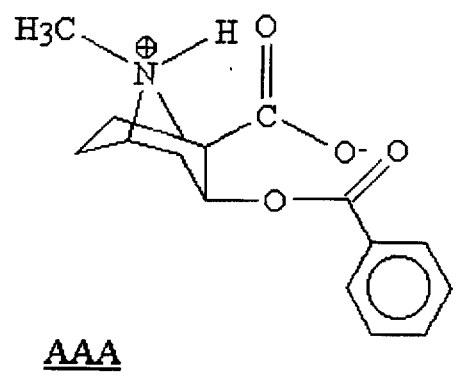
FIGS. 6 and 7 show show illustrative reagents needed to implement the method for the detection of Benzoylecgonine.
Figure 6:
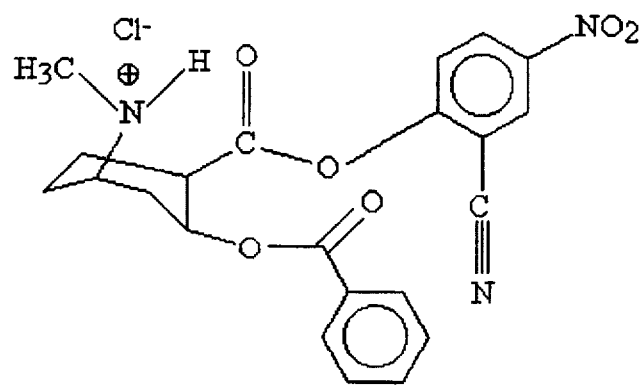
Figure 6:
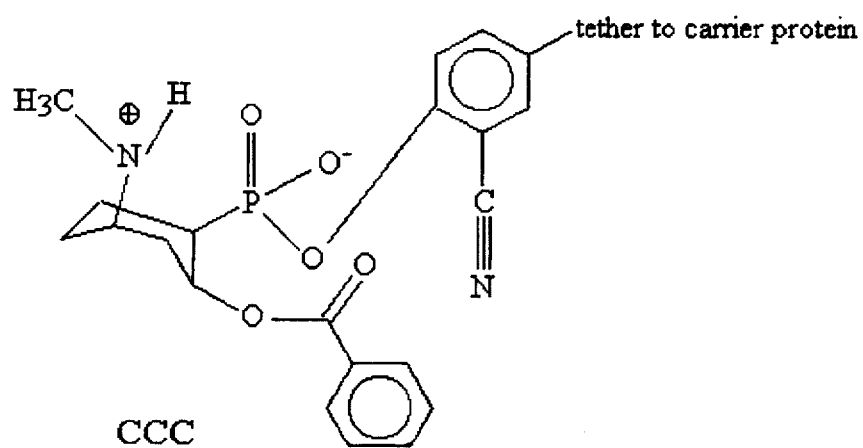

5A. Inhibition Assay (FIG. 6)

1. Designation of target molecule:
   Benzoyl ecgonine is the target molecule structure, AAA.
2. Synthesis of substrate molecule:
   The carboxylic acid group of benzoyl ecgonine is transformed to an ester linking the target molecule to a reporter molecule to provide the substrate molecule BBB. In this instance the reporter molecule is a chromophore:
3. Synthesis of transition state analog and generation of catalytic antibodies:
   A phosphonate ester CCC is synthesized as a transition-state analog for the carboxylic ester linking the target molecule carbonyl to the reporter molecule.
4. Screen for catalytic antibodies:
   Monoclonal antibodies generated against CCC are screened for catalytic activity against the substrate molecule BBB.
5. Screen for product analog inhibition:
   Catalytic monoclonal antibodies active against the substrate molecule BBB are screened for susceptibility to inhibition by the target molecule AAA.

Figure 7:
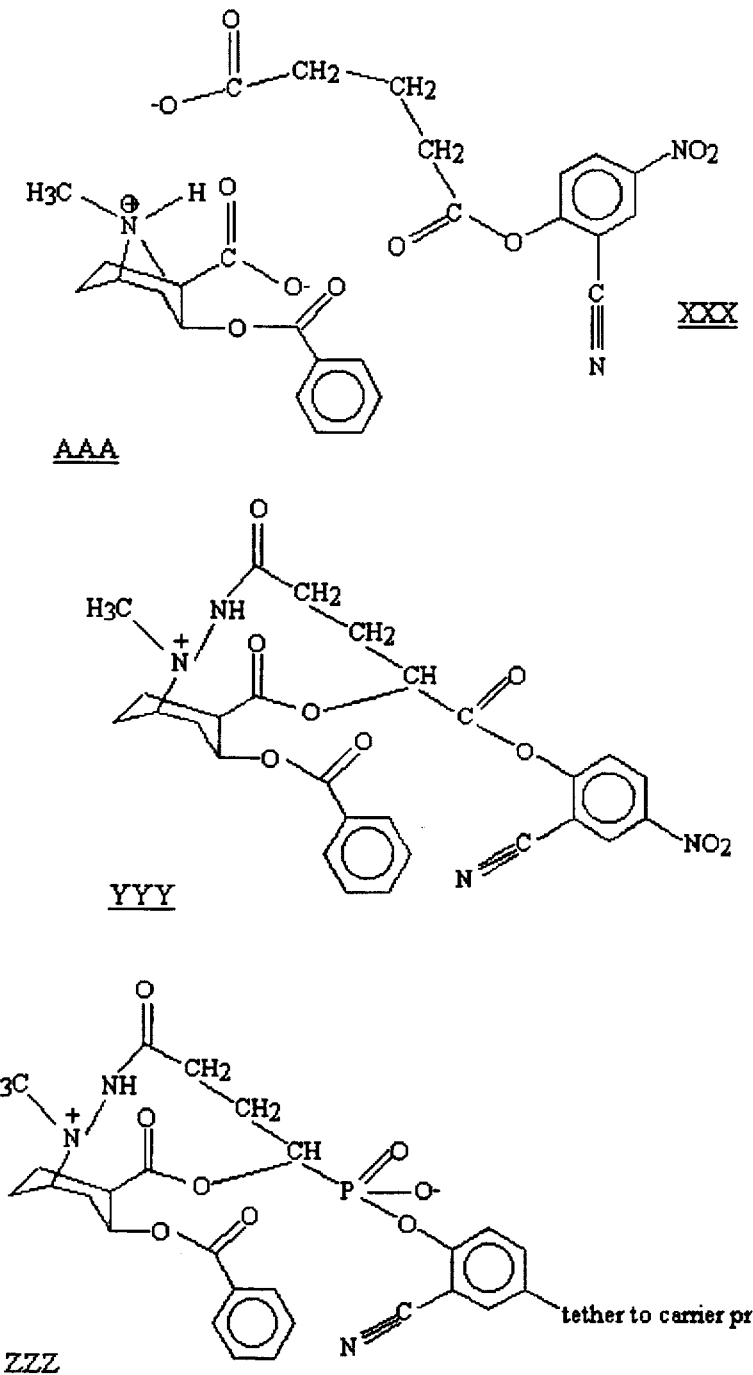

5B. Cofactor Assay (FIG. 7):

1. Target molecule designation:
   As above, the analyte benzoyl ecgonine is the target molecule structure AAA.
2. Design of target molecule-substrate molecule interaction:
   The charged ammonium group of benzoyl ecgonine provides a site for electrostatic interaction between target molecule AAA and a complementary substrate molecule XXX. The substrate molecule has a complementary binding domain connected by an ester linkage to a reporter molecule.
3. Synthesis of covalent version of target molecule substrate molecule interaction:
   The interaction of the carboxylate group of XXX and the alkyl ammonium of AAA can be mimicked by a covalently bound species YYY that retains the spacial orientation of the major (non-hydrogen) atoms.
4. Synthesis of the transition state analog:
   A transition state analog of YYY is constructed with a phosphonate monoester in place of the carboxylic acid ester attached to the reporter molecule to yield ZZZ.
5. Screen for target molecule dependent cMab hydrolysis of substrate molecule:
   Monoclonal antibodies to ZZZ are screened for those which hydrolyze YYY and those catalytic antibodies that hydrolyze YYY are screened for those that hydrolyze XXX only if AAA is present.

REFERENCES

1. U.S. Pat. No. 4,235,601, issued Nov. 25, 1980.
2. U.S. Pat. No. 4,205,952, issued Jun. 3, 1980.
3. U.S. Pat. No. 4,144,306, issued Mar. 13, 1979.
4. U.S. Pat. No. 4,175,923, issued Nov. 27, 1979.
5. U.S. Pat. No. 4,012,198, issued Mar. 15, 1977.
6. U.S. Pat. No. 4,012,198, issued Mar. 15, 1977.
7. U.S. Pat. No. 4,012,198.
8. U.S. Pat. No. 4,016,043, issued Apr. 5, 1977.
9. U.S. Pat. No. 4,038,485, issued Jul. 26, 1977.
10. U.S. Pat. No. 4,038,485, issued Jul. 26, 1977.
11. U.S. Pat. No. 4,094,677.
12. U.S. Pat. No. 4,235,601.
13. Tramontario, A., et al. Science 234:1566–1570, 1986.
14. Pollack, S. J., et al. Science 234:1570–1574, 1986.
15. Benkovic, S. J., et al. PNAS USA 85:5355–5358, 1988.
16. Jackson, D. Y., et al. J. Am. Chem. Soc. 110:4841–4842, 1988.
17. Benkovic, S. J., et al. Science 250:1135, 1990.
18. Janda, K. D., et al. Science 241:1188–1191, 1988.
19. Shokat, K. M., et al. Nature 338:269–271, 1989.
20. Iverson, B. L. and R. A. Lerner. Science 243:1184–1188, 1989.
21. Kitazume, T., et al. J. Am. Chem. Soc. 113:8573–8575, 1991.
22. Cochran, A. G., et al. J. Am. Chem. Soc. 113:6670–6672, 1991.
23. Janda, K. D., et al. J. Am. Chem. Soc. 113:291–297, 1991.
24. Tramontano, A., et al. PNAS 83:6736–6740, 1986.

25. Janda, K. D., et al. Science 244:437–440, 1989.

26. Tramontano, A., et al. J. Am. Chem. Soc. 110:2282–2286, 1988.

27. Janda, K. D., et al. J. Am. Chem. Soc. 113:5427–5434, 1991.

28. Baldwin, E., and P. G. Schultz. Science 245:1104–1107, 1989.

29. Janda, K. D., et al. Tetrahedron 47: 2503–2506, 1991.

30. Tawilk, D. S., et al. Proc. Natl. Acad. Sci. USA 90:373–377, 1993.

31. Benkovic, S. I., et al. Science 250:1135–1139, 1990.

32. Janda, K. D., et al. J. Am. Chem. Soc. 113:291–297, 1991.

33. Martin, M. T., et al. Biochemistry 30:9757–9761, 1991.

34. PCA/US88,04426 12 Dec. 1988. Chemical sensors employing catalytic antibodies 35. Rockefeller Foundation Science for Development Prize. The STD Diagnostics Challenge. 1994.

36. Mandell, R., et al. Principles and practice of infectious diseases, 3rd ed. Churchill Livingstone Inc., New York, 1990.

37. Benkovic et al. (1988) PNAS USA 85:5355–5358

38. Jones, H. M., et al. Journal of Infectious Diseases 166: 915–919, 1992.

39. Sillis, M., et al. Journal of Infection 25 (Supp. 1): 77–86, 1992.

40. Sternberg, K., et al. Culture, elisa and immunofluorescence tests for the diagnosis of conjunctivitis caused by chlamydia trachomatis in neonates and adults.

41. Gaydos, C. A., et al. Journal of Clinical Microbiology, 28(7): 1541–1544, 1990.

42. Magdner, L. S., et al. Journal of Clinical Microbiology. 28(4): 781–784, 1990.

43. Hallander, H., et al. Ear. J. Clin. Microbiol. Infect. Dis. 11: 550–552, 1992.

44. Zeeberg, B., et al. International Journal of STD & AIDS. 3: 355–359, 1992.

45. Stryer, Lubert, Biochemistry. W.H. Freeman and Company. New York, N.Y. 1988.

46. Wu, J. T., Annals of clinical and laboratory science. 21(2): 123–142, 1991.

47. Rosenberg, L. E. Inherited disorders of amino acid metabolism In E. Braunwald, K. J. Isselbacher, R. G. Petersdoff, L. D. Wilson, L. B. Martin, and A. S. Fauci. Harrison's principles of internal medicine, 11th ed. New York, McGraw-Hill, 1987:1611–1623.

48. American academy of pediatrics committee on genetics. Newborn screening fact sheets. Pediatrics. Vol 83(3): 449–464, 1989.

49. Seashore, M. R., Seminars in perinatology 14(6), 1990.

50. Mabry C. C., Annals of clinical and laboratory science. 20(6): 392–397, 1991.

51. Trefz, F. K., et al. Clinica Chimica Acta 217:15–21, 1993.

52. Whim, C. E. and R. J. Argauer. Fluorescence analysis a practical approach. New York, Marcel Dekker, Inc., 1970:334–354.

53. Cochran et al. (1988) J. Am. Chem. Soc. 110:7888–7890.

54. Green, B. S. (1989) Adv. Biotech. Processes 11:359–393.

55. Janda et al. (1988) J. Am. Chem. Soc. 110:4835–4837.

56. Chester, M. E., and W. M. Watkins, Biochem. Biophys. Res. Commun. 34:835, 1969.

57. Conchie, J and G. A. Levvy. Inhibition of glycosidases by aldonolactones. 65:389–395, 1956.

58. Cristina, L., et al. Medium effects in antibody-catalyzed reactions. Reports, 1019, 1991.

59. E. Harlow and D. Lane, eds., "Antibodies a laboratory manual" 1988, pages 567–577.

60. Near, R., 1995, Biotechniques 11:88–97; Glaser, S., et al. Borrebaeck, C. ed., In Antibody Engineering: A Practical Guide, 2nd Edition. W. H. Freeman and Co., New York.

61. Glaser, S. M., et al., 1992, I. Immunol. 149:3903–3913.

62. Huse, W. D., et al., 1992, J. Immunol. 149:3914–3920.

63. Carter, P. and J. A. Wells. Science p.394.

64. Iverson, B. L., and R. A. Lerner. Science 243:1184–1188, 1989.

65. Tramontario et al. (1988) J. Am. Chem. Soc. 110:2282–2286.

66. Pollack et al. (1986) Science 234: 1570–1573.

67. Schultz (1988) Science 240:426–433.

68. Cornish-Bowden (1979) Fundamentals of Enzyme Kinetics. Butterworths, London.

69. Segel, I. H. (1975) Enzyme Kinetics. Wiley, London.

70. Cleland, W. W. (1963) Biochim. Biophys. Acta, 67: 173.

71. Cleland, W. W. (1963) Nature 198:463.

72. Cleland, W. W. (1967) Adv. Enzymol. 29:1.

73. Stephens, R. S., et al. Infection and Immunity 47(3): 713–715, 1985.

74. Baehr, W., et al. PNAS USA 85:4000–4004, 1988.

75. Yuan, Y., et al., Infection and Immunity. 57(4): 1040–1049, 1989.

76. Peterson, E. M., et al. Infection and Immunity. 59(11): 4147–4153, 1991.

77. Conlan, J. W., et al. Molecular Microbiology. 3(3): 311–318, 1989.

78. Conlan, J. W., et al. Molecular Microbiology. 2(5): 673–679, 1988.

What is claimed is:

1. A method for determining the presence or absence of a target organic molecule in a sample which comprises:
   a. adding a substrate molecule to the sample,
   b. adding a catalytic monoclonal antibody to the sample which
      (i) recognizes and binds the target organic molecule when the target organic molecule is present in the sample, or
      (ii) recognizes, binds, and transforms the substrate molecule when the target organic molecule is not present in the sample; and
   c. detecting a change in the sample signifying the absence of the target organic molecule, the change being the production of a reporter molecule by an antibody-catalyzed reaction of the substrate molecule and thereby determining the presence or absence of the target organic molecule in the sample.

2. A method for determining the presence of a target organic molecule in a sample which comprises:
   a. adding a catalytic monoclonal antibody to the sample which (i) recognizes and binds the target organic molecule when the target organic molecule is present in the sample and (ii) recognizes, binds and transforms a substrate molecule when the target organic molecule is present in the sample;

b. adding a substrate which is the conjugate of a reporter molecule and a molecule which complements the target organic molecule through non-covalent bonding interactions;

c. detecting a change in the sample signifying the presence of the target organic molecule, the change being the production of the reporter molecule by an antibody-catalyzed reaction of substrate molecule and thereby determining the presence of target organic molecule in the sample.

3. The method of claim 1 or 2, wherein the target organic molecule is phenylalanine.

4. The method of claim 1 or 2, wherein the sample is derived from a cell sample.

5. The method of claim 1 or 2, wherein the sample is derived from a tissue sample.

6. The method of claim 1 or 2, wherein the sample is a biological fluid sample.

7. The method of claim 1 or 2, wherein the sample is from a human subject.

8. The method of claim 1 or 2, wherein the sample is from an animal subject.

9. The method of claim 8 wherein the animal subject is a dog, a horse, a cat, a cow or a pig.

10. The method of claim 1 or 2, wherein the reporter molecule is a detectable marker.

11. A method of claim 10, wherein the detectable marker contains a radioactive label.

12. A method of claim 11, wherein the radioactive label is $^{125}I$.

13. A method of claim 10, wherein the detectable marker is a colorometric marker.

14. A method of claim 10, wherein the detectable marker is a fluorometric marker.

15. A method of claim 10, wherein the detectable marker is a chemiluminescent or bioluminescent marker.

16. A method of claim 10, wherein the detectable marker is the product of an enzymatic reaction.

17. The method of claim 1 or 2, wherein the catalytic monoclonal antibody recognizes and binds phenylpyruvate.

18. The method of claim 1 or 2, wherein the change is a visual change.

19. The method of claim 18, wherein the visual change is a change in the color of the sample.

20. A method of claim 1 or 2, wherein the catalytic monoclonal antibody is bound to a matrix.

21. A method of claim 20, wherein the matrix is agarose or sepharose.

22. A method of claim 1 or 2, wherein the catalytic monoclonal antibody is bound to a tube.

23. A method of claim 1 or 2, wherein the catalytic monoclonal antibody is bound to a bead.

24. A method for diagnosing in a subject a disease condition associated with the presence of an organic molecule which comprises determining in a sample from the subject the presence of the organic molecule in accordance with the method of claim 1 or 2, the presence of the organic molecule indicating the presence of the disease condition.

25. A method for monitoring the course of a disease condition in a subject which comprises determining in a first sample from the subject the presence of an organic molecule according to the method of claim 1 or 2 and comparing the amount so determined with the amount present in a second sample from the subject, such samples being taken at different points in time, a difference in the amounts determined being indicative of the course of the disease condition.

* * * * *